(12) United States Patent
Simpson et al.

(10) Patent No.: US 9,539,149 B2
(45) Date of Patent: *Jan. 10, 2017

(54) SUPERHYDROPHOBIC, DIATOMACEOUS EARTH COMPRISING BANDAGES AND METHOD OF MAKING THE SAME

(75) Inventors: John T. Simpson, Clinton, TN (US); Brian R. D'Urso, Pittsburgh, PA (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 1675 days.

This patent is subject to a terminal disclaimer.

(21) Appl. No.: 12/273,823

(22) Filed: Nov. 19, 2008

(65) Prior Publication Data

US 2010/0286582 A1 Nov. 11, 2010

Related U.S. Application Data

(63) Continuation-in-part of application No. 11/777,486, filed on Jul. 13, 2007, now Pat. No. 8,216,674.

(51) Int. Cl.
*A61F 13/00* (2006.01)
*B05D 5/00* (2006.01)
(Continued)

(52) U.S. Cl.
CPC ......... *A61F 13/0289* (2013.01); *A61F 13/022* (2013.01); *A61L 15/40* (2013.01);
(Continued)

(58) Field of Classification Search
None
See application file for complete search history.

(56) References Cited

U.S. PATENT DOCUMENTS 3,931,428 A * 1/1976 Reick ............................ 428/149
4,326,509 A 4/1982 Usukura
(Continued)

FOREIGN PATENT DOCUMENTS

DE 19950106 4/2001
EP 0171168 2/1986
(Continued)

OTHER PUBLICATIONS

Whelan, Tony, Polymer Technology Dictionary, pub. 1994, Chapman & Hall, pp. 395.*

(Continued)

*Primary Examiner* — Cheng Huang
(74) *Attorney, Agent, or Firm* — Fox Rothschild LLP

(57) ABSTRACT

A bandage comprising a substrate having a first surface with a plurality of superhydrophobic particles attached to the first surface. The plurality of superhydrophobic particles can be porous diatomaceous earth particles having a hydrophobic layer conforming to the surfaces of the DE particles, where the hydrophobic layer is bound to the DE particles. The plurality of attached superhydrophobic particles can render the first surface superhydrophobic, while a second surface opposite the first surface can be hydrophilic or hydrophobic. The substrate can be breathable in order to maintain skin health for the tissue underlying the bandage. The substrate can be selected from porous films, apertured films, textiles, nonwoven materials, impregnated composites thereof, and combinations thereof.

19 Claims, 3 Drawing Sheets

(51) Int. Cl.
*A61F 13/02* (2006.01)
*A61L 15/40* (2006.01)
*A61L 15/42* (2006.01)
*D06M 11/79* (2006.01)
*D06M 15/19* (2006.01)
*D06M 23/08* (2006.01)
*D06M 23/10* (2006.01)

(52) U.S. Cl.
CPC ............. *A61L 15/42* (2013.01); *D06M 11/79* (2013.01); *D06M 15/19* (2013.01); *D06M 23/08* (2013.01); *D06M 23/10* (2013.01); *A61F 2013/004* (2013.01); *A61F 2013/00255* (2013.01); *A61F 2013/00319* (2013.01); *A61F 2013/00863* (2013.01); *A61F 2013/00885* (2013.01); *A61F 2013/00889* (2013.01); *D06M 2200/12* (2013.01)

(56) References Cited

U.S. PATENT DOCUMENTS

| | | | |
|---|---|---|---|
| 5,086,764 | A | 2/1992 | Gilman |
| 5,154,928 | A | 10/1992 | Andrews |
| 5,258,221 | A | 11/1993 | Meirowitz |
| 5,458,976 | A | 10/1995 | Horino et al. |
| 5,733,365 | A | 3/1998 | Halko et al. |
| 6,040,251 | A | 3/2000 | Caldwell |
| 6,360,068 | B1 | 3/2002 | Kinoshita et al. |
| 6,384,293 | B1 | 5/2002 | Marcussen |
| 6,410,630 | B1 | 6/2002 | Hoover et al. |
| 6,512,072 | B1 * | 1/2003 | Gantner et al. ................. 528/34 |
| 6,528,220 | B2 | 3/2003 | Yoshida et al. |
| 6,743,842 | B1 | 6/2004 | Fukagawa et al. |
| 6,800,412 | B2 | 10/2004 | Sugiyama et al. |
| 6,887,636 | B2 | 5/2005 | Matsuda et al. |
| 6,916,301 | B1 | 7/2005 | Clare |
| 6,936,390 | B2 | 8/2005 | Nanya et al. |
| 7,020,899 | B1 | 4/2006 | Carlopio |
| 7,098,145 | B2 | 8/2006 | Fukushima et al. |
| 7,110,710 | B2 | 9/2006 | Yamashita et al. |
| 7,129,013 | B2 | 10/2006 | Higuchi et al. |
| 7,265,256 | B2 | 9/2007 | Artenstein |
| 2002/0164419 | A1 | 11/2002 | Fukushima et al. |
| 2004/0067247 | A1 | 4/2004 | De Sloovere et al. |
| 2005/0009953 | A1 | 1/2005 | Shea |
| 2005/0010154 | A1 * | 1/2005 | Wright et al. ................. 602/58 |
| 2005/0136242 | A1 * | 6/2005 | Yahiaoui et al. .......... 428/317.9 |
| 2006/0008678 | A1 | 1/2006 | Fukushima et al. |
| 2006/0019042 | A1 | 1/2006 | Nojima et al. |
| 2006/0024508 | A1 | 2/2006 | D'Urso et al. |
| 2006/0113618 | A1 | 6/2006 | Reboa |
| 2006/0246277 | A1 | 11/2006 | Axtell, III |

FOREIGN PATENT DOCUMENTS

| | | |
|---|---|---|
| EP | 0927748 | 7/1999 |
| GB | 1154835 | 6/1969 |

OTHER PUBLICATIONS

Faulde et al., Toxic and behavioural effects of different modified diatomaceous earths on teh German cockroach, J. Stored Prod. Res., vol. 42, No. 3, pp. 253-263 (Jan. 1, 2006).

Bankovic et al., Obtention of selective membranes for water and hydrophobic liquids by plasma enhanced chemical vapor deposition on porous substrates, Mat. Sci. & Eng. B, vol. 112, No. 2-3, pp. 165-170 (Sep. 25, 2004).

Dolley, Diatomite, U.S. Geological Survey Minerals Yearbook, pp. 24.1-24.6 (1999).

Yuan et al., The hydroxyl species and acid sites on diatomite surface: a combined IR and Raman study, App. Surface Sci., 227, pp. 30-39 (2004).

3M, Nexcare Bandages, http://solutions.3m.com/wps/portal/3M/en_CA/Nexcare/Home/Products/Bandages/Waterproof/, printed Aug. 28, 2009.

* cited by examiner

SUPERHYDROPHOBIC, DIATOMACEOUS EARTH COMPRISING BANDAGES AND METHOD OF MAKING THE SAME

CROSS-REFERENCE TO RELATED APPLICATIONS

This application is a continuation-in-part of U.S. patent application Ser. No. 11/777,486, "Superhydrophobic Diatomaceous Earth," filed Jul. 13, 2007, now U.S. Pat. No. 8,216,674 the entirety of which is incorporated herein by reference.

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

FIELD OF THE INVENTION

The present invention relates to bandages having hydrophobic or superhydrophobic surfaces and methods of making the same.

BACKGROUND OF THE INVENTION

Bandages have long been used to support tissue and to aid wound healing. In order to allow the skin covered by a bandage to undergo transpiration it is important that the bandage is breathable. A disadvantage of current breathable bandages is that use of breathable materials results in a propensity to absorb water. This problem becomes acute when the wearer attempts to wash adjacent skin or take a shower and ends up saturating the bandage or the underlying dressing with water. Once the bandage is saturated it is necessary for the individual to re-bandage or re-dress the injury. This problem is even more pronounced with orthopedic casts, which are worn for weeks or months.

SUMMARY OF THE INVENTION

A breathable bandage having superhydrophobic particles attached to a surface thereof to prevent water from penetrating from the exterior to the interior of the bandage. The bandage can include a substrate comprising a first surface, and a plurality of superhydrophobic particles attached to the first surface. The plurality of superhydrophobic particles can be porous diatomaceous earth (DE) particles having a hydrophobic layer conforming to surfaces of the DE particles. The conforming hydrophobic layer can be bound to the DE particles.

The plurality of attached superhydrophobic particles can render the first surface of the substrate superhydrophobic. The substrate can have a second surface, opposite the first surface, that is not superhydrophobic. The substrate can have a second surface, opposite the first surface, that is hydrophilic.

The bandage can also include a binder adhering the plurality of superhydrophobic particles to the first surface. The plurality of superhydrophobic particles can be mechanically bound to the first surface.

The substrate can be breathable. The substrate can be selected from the group consisting of porous films, apertured films, textiles, nonwoven materials, impregnated composites thereof, and combinations thereof.

The bandage can also include a dressing or an absorbent material attached to the material. The dressing or absorbent material can be attached to a side of the substrate opposite the first surface. The bandage can be a bandage selected from the group consisting of an adhesive bandage, a compression bandage, a wrap, gauze, medical tape, an orthopedic cast, and combinations thereof.

The invention also includes a method of making a bandage having a water repellant surface. The method includes providing a substrate and attaching a plurality of particles to a first surface of the substrate. A plurality of superhydrophobic particles can be formed from a plurality of particles. The plurality of superhydrophobic particles can be porous DE particles having a hydrophobic layer conforming to surfaces of the DE particles. The hydrophobic layer can be bound to the DE particles.

The first surface of the substrate can be hydrophobic after the method is complete. The plurality of attached superhydrophobic particles can render a first surface of the substrate superhydrophobic. The plurality of particles can be applied to the first surface while the first surface is adherent, e.g., tacky.

The attaching step can include forming a mixture of the plurality of particles and a solvent, and applying the mixture to the first surface. The solvent can be volatile at a temperature of the applying step, and the first surface can be soluble in the solvent. The attaching step can include forming a mixture including a plurality of particles and an adhesive, and applying the mixture to the first surface.

The step of forming the superhydrophobic particles can occur before or after the attaching step. The material can include a second surface, opposite the first surface, that is hydrophilic after the method is complete.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

In one embodiment, the invention can be a breathable bandage having a superhydrophobic surface. The superhydrophobic surface can prevent water from penetrating through the exterior of the bandage, while allowing water vapor from the skin to escape through the bandage. Thus, the breathable bandage can be breathable in order to facilitate proper healing and skin health, while preventing water from penetrating the bandage and wetting bandage layers closer to the skin.

Figure 1:
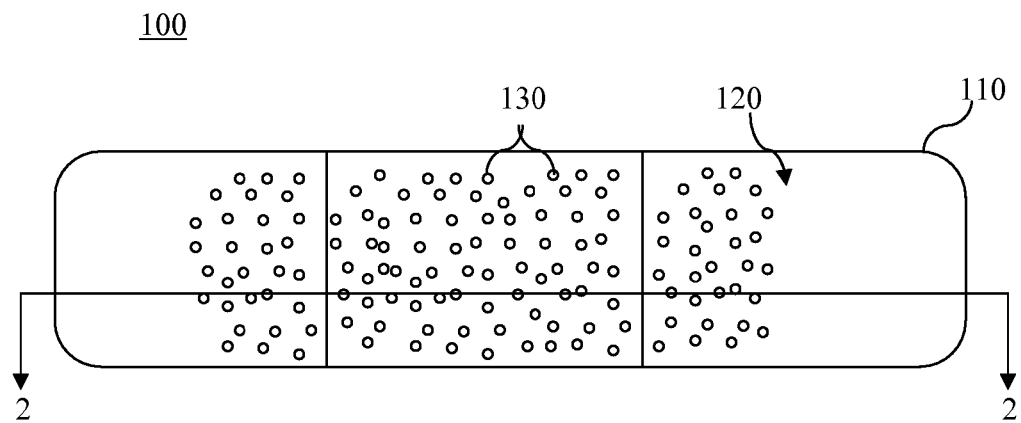
FIG. 1 is a top view of an adhesive bandage according to the invention.
Figure 2:
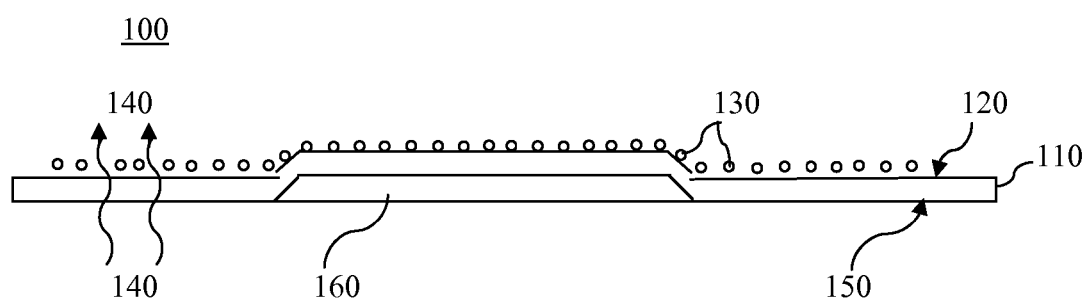
FIG. 2 is a cross-sectional view of the adhesive bandage of FIG. 1 taken along cut line 2-2.

As shown in FIGS. 1 and 2, in one embodiment, the invention can be a bandage 100 that includes a substrate 110 having a first surface 120 and a plurality of superhydrophobic DE particles 130 attached to the first surface 120. The plurality of superhydrophobic particles can be porous DE particles having a hydrophobic layer conforming to surfaces of the DE particles. The conforming hydrophobic layer can be bound to the DE particles. The substrate can be breathable.

Is used herein, "superhydrophobic" is used to refer to a substrate or surface having a contact angle with water of at least 150 degrees. For example, the superhydrophobic materials disclosed herein can have a contact angle of at least 155 degrees, at least 160 degrees, at least 165 degrees, at least 170 degrees or at least 175 degrees.

As used herein, "attached" includes physical and chemical attachment. For example, a particle can be attached to gauze where it is physically entangled in fibers forming the gauze. A particle can also be attached to a surface where the particle is bound by adhesive to the surface. In some embodiments, the adhesive can be the surface itself, such as where the particle is applied to the surface in a mixture with a volatile solvent that flash melts the surface.

The plurality of superhydrophobic DE particles 130 can be mechanically bound to the first surface 120. The plurality of superhydrophobic DE particles 130 can be chemically bound to the first surface 120. A superhydrophobic DE particle is chemically bound to the first surface both where the superhydrophobic DE particle is directly chemically bound to the first surface and where the superhydrophobic DE particle is chemically bound to a binder, or other intermediate layer, that is bound to the first surface. Similarly, a superhydrophobic DE particle is mechanically bound to the first surface both where the superhydrophobic DE particle is directly mechanically bound to the first surface and where the superhydrophobic DE particle is mechanically bound to a binder, or other intermediate layer, that is bound to the first surface.

As used herein, "breathable" is used to refer to a substrate or bandage that is permeable to water vapor and gases. For example, as shown in FIG. 2, water vapor 140 can pass through a breathable bandage 100 made from a breathable substrate 110. Breathability can be measured using water vapor transmission rate (WVTR) measurements, such as that set forth in ASTM Standard E96-80. A breathable substrate can have a WVTR of at least about 50 g/m$^2$/day, at least about 100 g/m$^2$/day, at least about 200 g/m$^2$/day, at least about 300 g/m$^2$/day, or even at least about 500 g/m$^2$/day.

The plurality of attached superhydrophobic DE particles can render the first surface of a substrate superhydrophobic. The substrate 110 can have a second surface 150, opposite the first surface 120, that is not superhydrophobic. The second surface 150 can even be hydrophilic. In an embodiment such as that shown in FIG. 2, it can be useful for the second surface to be hydrophilic where the second surface 150 is in contact with a dressing 160 and the first surface 120 forms the bandage 100 exterior, which is in contact with the environment. The second surface 150 of the substrate 110 can also be hydrophobic or even rendered superhydrophobic using the methods disclosed herein.

The bandage can also include a binder, i.e., adhesive, for adhering the plurality of superhydrophobic DE particles to the first surface (not shown). The binder can be any binder useful for adhesion of the superhydrophobic DE particles to the target substrate. In some instances, the DE particles can be attached to the substrate while in a hydrophilic or hydrophobic state and converted to a superhydrophobic state only after the binder is used to adhere the particles to the first surface. The ability to attach particles in either a hydrophobic or hydrophilic state greatly expands the number of binders that may be useful for adhering the superhydrophobic DE particles to the first surface.

Exemplary binders for adhering superhydrophobic DE particles to the first surface include, but are not limited to, polypropylene; polystyrene; polyacrylate; cyanoacrylates; amorphous fluoropolymer, such as that sold by E. I. du Pont de Nemours and Company ("DuPont") under the TEFLON AF® trademark; acrylic copolymer and alkyd resin mixtures, such as those sold by Rohm and Haas under the FASTRACK XSR® trademark. Exemplary binders for adhering hydrophilic or hydrophobic particles include, but are not limited to, polycyanoacrylates, polyacrylates, polysiloxanes, polyisobutylene, polyisoprene, styrenes, polyvinylpyrrolidone, polyvinyl alcohol, styrene block copolymers, block amide copolymers, and copolymers and mixtures thereof. The binders can include further components, including tackifiers, plasticizers and other components typically found in binders.

One consideration for producing the claimed bandages is that the unique topography of the DE particles enhances the superhydrophobic nature of the DE particles. In order to produce the desired superhydrophobic substrate surface, the particle-binder mixture should be formulated to avoid coating of the topography of the DE particles by the binder in a manner that substantially diminishes the topography of the DE particles. One method of achieving this objective is to dilute the binder mixture with an appropriate solvent, such as an organic solvent. The organic solvent can be, but is not necessarily, volatile at room temperature, e.g., 22-25° C. Organic solvents that can be useful include, but are not limited to acetone, methyl ethyl ketone, ethyl acetate, toluene, methyl isobutyl ketone, tetrahydrofuran, cyclohexanone, methanol, n-propanol, n-hexane, and perfluorinated liquids. Exemplary perfluorinated liquids can be obtained from 3M Company under the FLUORINERT® trademark.

It can be desirable for the distribution of the superhydrophobic particles in the mixtures described herein to be as homogeneous as possible. Homogeneity of the superhydrophobic particles can be enhanced by use of a dispersant to prevent the superhydrophobic particles from agglomerating in the mixture. Exemplary dispersants include hexanes, ethanol, acetone, isopropyl alcohol, and FLUORINERT®, such as FC-40 and FC-75. In addition, a mechanical means, such as sonication, can also be used to induce dispersion of these superhydrophobic particle comprising solutions and mixtures.

The bandage substrate can be selected from the group consisting of porous or perforated films, textiles, nonwoven materials, impregnated composites thereof, and combinations thereof. The bandage substrate can be an elastic material, such as a woven material containing elastomeric fibers, or a laminate of one or more bandage layers with one or more elastomeric layers. Impregnated composites can include orthopedic casts and similar bandages. As used herein, the term bandage is intended to include wraps that are applied over existing bandages in order to prevent saturation of the underlying bandage.

As shown in FIG. 2, the bandage 100 can include a dressing or absorbent material 160 attached to the substrate 110. The dressing 160 can be adjacent to a second surface 150 of the substrate 110 opposite the first surface 120. The bandage can be any bandage including, but not limited to, an adhesive bandage, a compression bandage, a wrap, gauze, medical tape, an orthopedic cast, and combinations thereof.

In another embodiment, the invention includes a method of making a bandage having a water repellant surface. The method can include providing a substrate, attaching a plurality of DE particles to a first surface of the substrate, and forming a plurality of superhydrophobic DE particles from a plurality of DE particles. The plurality of superhydrophobic particles can be porous diatomaceous earth (DE) particles having a hydrophobic layer conforming to surfaces of the DE particles. The conforming hydrophobic layer can be bound to the DE particles. The complete method can produce a first surface of the substrate that is hydrophobic after the method is complete. The complete method can produce a first surface that is superhydrophobic after the method is complete. A second surface opposite the first surface can be hydrophilic after the method is complete.

The attaching step can include forming a mixture comprising the plurality of particles and a solvent and applying the mixture to the first surface of the substrate. The amount of DE particles in a mixture can generally range from 0.2 wt-% to 10 wt-%, or between 0.5 wt-% to 8 wt-%.

An exemplary mixture can be a solution containing 1 wt-% superhydrophobic DE particles in a solvent, e.g., ethanol. A porous substrate, such as a gauze, could be dipped in the ethanol-superhydrophobic DE particle mixture and then removed. Once the ethanol evaporates, the resulting gauze substrate can be rendered superhydrophobic by the presence of superhydrophobic DE particles entangled in the gauze. Similarly, a solution of superhydrophobic particles and acetone could be sprayed onto a bandage material, such as an orthopedic cast, and the acetone allowed to evaporate.

The attaching step can be a "flash melting" step where the solvent is volatile at the applying step temperature and the first surface is soluble in the solvent. In such an embodiment, the first surface can be a polymer that is soluble in the solvent. The first surface can begin to solubilize into the mixture as the solvent is volatilizing into the atmosphere. Evaporation of the solvent can cause the solubilized portion of the first surface to precipitate over a portion of the superhydrophobic particles, thereby attaching the particles to the first surface.

Examples of flash melting include a solution of acetone and 1 wt-% superhydrophobic DE particles applied to a polypropylene bandage material. Another example includes applying to a polyvinylchloride containing material a solution of 1 wt-% superhydrophobic DE particles in tetrahydrofuran, methyl ethyl ketone and, optionally, cyclohexanone. A mixture of tetrahydrofuran, methyl ethyl ketone and, optionally, cyclohexanone is sold as PVC Primer and can be purchased from numerous companies, including Cantex, Inc.

In another embodiment, the attaching step can include forming a mixture comprising the plurality of particles and an adhesive, and applying the adhesive mixture to the first surface. The binder can be applied as a polymer, e.g., polypropylene, polystyrene, dissolved in a solvent. As noted above, a solvent, a dispersant, a diluent, or any combination can be added to the DE particle-adhesive mixture in order to produce the desired superhydrophobic surface.

The adhesive mixture can include 1 wt-% superhydrophobic DE particles and 0.1 wt-% cyanoacrylate monomer in acetone. Another adhesive mixture can include 1 wt-% superhydrophobic DE particles and 0.1 wt-% polypropylene in acetone. Yet another adhesive mixture can include 1 wt-% superhydrophobic DE particles and 0.1 wt-% amorphous fluoropolymer, such as TEFLON AF® sold by DuPont, in a perfluorinated solvent, such as FLUORINERT® available from 3M Corp. Another adhesive mixture is 1 wt-% superhydrophobic DE particles and 0.1 wt-% of an acrylic copolymer and alkyd resin mixture, such as that sold by Rohm and Haas under the FASTRACK XSR® trademark, in acetone.

The mixtures described above can be applied to the substrate using any appropriate techniques including, but not limited to, dipping, painting, printing, and spraying. For example, the mixture can be printed onto the substrate using a gravure roll or an inkjet-type print head.

In another embodiment, the attaching step can include applying the plurality of particles to the first surface while the first surface is adherent. For example, superhydrophobic DE particles can be sprinkled onto the surface of an orthopedic cast while the exterior of the cast is still drying. Another example, would be to apply superhydrophobic DE particles to the surface of an extruded substrate shortly after extrusion from the die tip and prior to quenching. In both cases, the superhydrophobic DE particles are applied to the first surface while the substrate is still adherent, thereby producing a bandage with superhydrophobic DE particles directly attached to the surface of the substrate.

The forming step can occur either before or after the attaching step. This provides flexibility regarding any number of features of the method. For example, treating the DE particles to form superhydrophobic DE particles after the attaching step allows use of a broad range of aqueous solvents for the attaching step. A benefit of forming the superhydrophobic DE particles prior to attachment is that the other elements of the bandage are not exposed to the moieties used to add the hydrophobic functionality to the superhydrophobic particles.

The coated superhydrophobic DE powders and the process for forming these powders is now described in more detail. The coated powders comprise a plurality of porous DE particles where the processed porous DE particles have little or no organic contamination and where the particles retain the surface topography and silicate surface functionalities of natural DE. The surface topography of natural DE is highly partitioned with ridges and peaks extending outward from the particle. The silicate surface is that of amorphous silica where numerous silanol, Si—OH groups are surface terminal groups of the silicate network. When the organic contaminant level of the DE is very low, as with some food grade DE, a heat treatment does not have to be carried out to remove organic contaminants.

The DE particles preferably undergo a heat treatment to assure that organic impurities are substantially removed. The heat treatment is carried out in a controlled temperature range, below 650° C., selected such that organic impurities are thermally decomposed and lost as volatiles without producing excessive heat, which can damage the surface topography or significantly decrease the amount of silanol functionality at the surface. The heat treatment also removes water from the surface of the DE. A hydrophobic coating can then be disposed on surfaces of the DE particles. A preferred form of coating is a hydrophobic self-assembled monolayer (SAM).

Diatomaceous earth is a chalk-like, soft, friable, earthy, very fine-grained, siliceous sedimentary rock usually light in color, although white when pure. It is very finely porous and is very low in density, such that it floats on water until its surface is wetted. Diatomaceous earth is chemically inert in the presence of most liquids and gases. It also displays low thermal conductivity and a high fusion point. Many sediments and sedimentary rocks are somewhat diatomaceous. The deposits result from an accumulation in oceans or fresh waters of the amorphous silica (opal, $SiO_2.nH_2O$) cell walls of dead diatoms, which are microscopic single-cell aquatic plants (algae). The fossilized skeletal remains—a pair of shells (frustules)—vary in size from less than 1 micron to more than 1 millimeter but are typically 10 to 200 microns across. The frustules have a broad variety of delicate, lacy, perforated shapes ranging from discs and balls to ladders, feathers, and needles. This variety of shapes produces the partitioned surface of DE that provides the surface topography conducive to the superhydrophobic properties of the present invention. The typical chemical composition of diatomaceous earth is about 86% silica, 5% sodium, 3% magnesium and 2% iron.

DE is generally processed into two different products: natural-grade (or uncalcined) and calcined. The processing of natural-grade diatomite consists of crushing and drying. Crude diatomite commonly contains up to 40 percent moisture and can include more that 60 percent water. Typically a primary crushing is carried out on the as-mined material to yield a desired aggregate size. The crushed DE is subsequently milled and dried simultaneously where suspended particles of diatomite are carried in a stream of hot gases. Flash and rotary dryers are used to dry the material to a powder of approximately 15 percent moisture. Typical flash dryer operating temperatures range from 70 to 430° C. The suspended particles exiting the dryer pass through a series of fans, cyclones, and separators. These sequential operations separate the powder into various sizes, remove waste impurities, and expel the absorbed water. These natural-milled diatomite products are then bagged or handled in bulk without additional processing. Natural-grade DE is preferred for the practice of the invention.

For filtration uses, natural grade diatomite is calcined by heat treatment in gas- or fuel oil-fired rotary calciners, with or without a fluxing agent. Straight calcining is used for adjusting the particle size distribution for use as a medium flow rate filter aid. The product of straight calcining has a pink color from the oxidation of iron in the raw material, which is more intense with increasing iron oxide content of the DE. Typical calciner operating temperatures range from 650 to 1,200° C. For straight-calcined grades, the powder is heated in large rotary calciners to the point of incipient fusion, and thus, in the strict technical sense, the process is one of sintering rather than calcining.

DE treated in excess of 650° C. undergoes material and structural changes which is deleterious to the silicate surface functionality, e.g., silanol groups, to which the hydrophobic coating of the present invention is ultimately bound and can be deleterious to the highly partitioned surface topography that enables superhydrophobic character when coated with a hydrophobic material. The surface of uncalcined DE is that of amorphous silica, more similar in composition to that of precipitated silica rather than pyrogenic silica. There is a reasonably high silanol content to the DE surface that can be characterized as having strong hydrogen bonded silanols, moderate strength hydrogen bonded silanols and weak hydrogen bonded silanols. Upon heating to 650° C., nearly all strongly hydrogen bonded silanols are lost, moderate strength hydrogen bonded silanols are lost at a temperature of approximately 1,000° C., and above 1,000° C. the weak hydrogen bonded silanols are lost. For the practice of the invention it is desirable that although surface bound water is reduced to a low level or completely removed, the presence of at least some moderate strength hydrogen bonded silanols is intended to provide sufficient sites for bonding of the coating layer and thereby stabilizing the hydrophobic self-assembled monolayer coating. For this reason calcined DE is generally avoided for the practice of the invention as most calcined DE has been treated in excess of 800° C. The desired surface topography formed by the diatoms and a sufficient amount of silanol functionality on the silicate surface to achieve the continuous SAM of the present invention is generally unavailable with DE that is heat treated in excess of 800° C.

Figure 3:
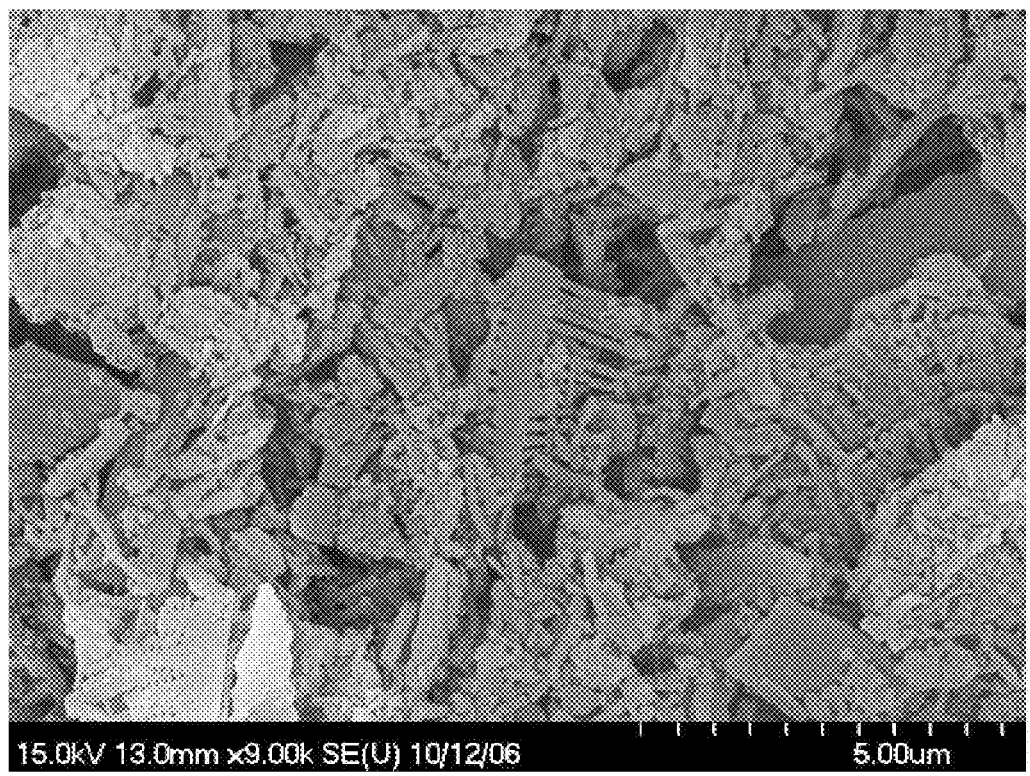
FIG. 3 is a Scanning Electron Microscope (SEM) image of DE as used in the invention displaying a collection of randomly shaped and sized particles of less than 3 μm in cross-section, where the average particle is less than 1 μm in cross-section and the surfaces of the particles display a partitioning of the surface.

For the practice of the invention the uncalcined DE is treated by heating to temperatures of about 450 to about 700° C., preferably 500 to 600° C., under a dry gas stream or under vacuum prior to applying the hydrophobic coating to the surface. FIG. 3 shows a SEM image of a collection of DE particles as used in the invention. As can be seen in FIG. 3, where the distance between marks on the scale is 500 nm, the crushed DE displays particles where the cross-section is less than 3 µm and the average cross-section is less than 1 µm. These nanoparticles have irregular features with a partitioning of the surface to features of about 100 nm in width and less. The temperature and time of heating depends on the DE as received and the structure of the hydrophobing reagent and the hydrophobing protocol employed. The heat treatment removes organic impurities that can interfere with the deposition of a hydrophobic layer. The heat treatment also removes water from the surface to an extent that the partitioned features of the DE topography are not significantly filled with water. Presence of the water in the voids between the DE features can prevent hydrophobic coatings from conforming to the silicate surface topography displayed by the natural-grade DE which provides the partitioned features of that topography that permits the development of a superhydrophobic surface upon coating with a hydrophobic material. Small amounts of water can be present for practice of the invention as long as the water does not prevent the hydrophobic coating material from conforming to the DE surface.

The hydrophobic material is continuous, such that the portion of the solid surface that will encounter a water bead is covered with the hydrophobic material. Surfaces sufficiently remote from where the water will contact the hydrophobic DE need not be covered with the hydrophobic coating, however, the uncoated surfaces should not physically or chemically bind to water and promote displacement of the air in the voids with water. Generally, the hydrophobic coating will continuously coat the DE surface, and the coating is preferably formed as a self assembled monolayer. Self assembled monolayers (SAMs) are surfaces consisting of a single layer of molecules on a substrate where the molecule can readily arrange in a manner where a head group is directed or adhered to a surface, generally by the formation of at least one covalent bond, and a tail group is directed to the air interface to provide desired surface properties, such as hydrophobicity in the present invention. As the hydrophobic tail group has the lower surface energy it dominates the air surface interactions providing a continuous surface of tail groups.

SAM application methods are advantageous over alternate surface treatment techniques that can be used in the practice of the invention. Exemplary SAM application methods can include chemical vapor deposition and molecular beam epitaxy. Generally, molecular beam epitaxy can be used where more exotic conditions and equipment is required to add hydrophobic coatings to the DE surfaces of the invention. SAMs of the present invention can be prepared by adding a melt or solution of the desired SAM precursor onto the substrate surface where at least a sufficient concentration of SAM precursor is present to achieve a continuous conformal monolayer. After the hydrophobic SAM is formed and fixed to the DE surface, any excess precursor can be removed by a volatizing or washing step. In this manner the SAM air interface can be primarily or exclusively dominated by the hydrophobic moiety.

One example of a SAM precursor which can be used in an embodiment of the invention is tridecafluoro-1,1,2,2-tetrahydroctyltriclorosilane. This molecule undergoes condensation with the silanol groups of the DE surface releasing HCl and bonding the tridecafluoro-1,1,2,2-tetrahydroctylsilyls group to the surface of the heat treated DE via a Si—O covalent bond. The tridecafluorohexyl moiety of the tridecafluoro-1,1,2,2-tetrahydroctylsilyl groups attached to the DE surface provide a monomolecular layer that has a hydrophobicity similar to polytetrafluoroethylene. Hence, by the use of such SAMs, the DE retains the desired partitioned surface structure while rendering that partitioned surface hydrophobic by directing the perfluorohexyl moiety to the air interface thereby yielding the desired superhydrophobic powder.

A non-exclusive list of exemplary SAM precursors that can be used for various embodiments of the invention is:

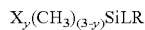

where y=1 to 3; X is Cl, Br, I, H, HO, R'HN, R'$_2$N, imidizolo, R'C(O)N(H), R'C(O)N(R"), R'O, F$_3$CC(O)N(H), F$_3$CC(O)N(CH$_3$), or F$_3$S(O)$_2$O, where R' is a straight or branched chain hydrocarbon of 1 to 4 carbons and R" is methyl or ethyl; L, a linking group, is CH$_2$CH$_2$, CH$_2$CH$_2$CH$_2$, CH$_2$CH$_2$O, CH$_2$CH$_2$CH$_2$O, CH$_2$CH$_2$C(O), CH$_2$CH$_2$CH$_2$C(O), CH$_2$CH$_2$OCH$_2$, CH$_2$CH$_2$CH$_2$OCH$_2$; and R, a hydrophobic moiety, is (CF$_2$)$_n$CF$_3$ or (CF(CF$_3$)OCF$_2$)$_n$CF$_2$CF$_3$, where n is 0 to 24. Preferred SAM precursors have y=3 and are commonly referred to as silane coupling agents. Some useful SAM precursors include y=3, X═Cl, L═CH$_2$CH$_2$, and R═(CF$_2$)$_n$CF$_3$; and y=3, X═Cl, L═CH$_2$CH$_2$ and R═(CF2)$_5$CF$_3$.

Where y>1 the SAM precursors can attach to multiple OH groups on the DE surface and can become linked together with the consumption of water, either residual on the surface, formed by condensation with the surface, or added before, during or after the deposition of the SAM precursor. All SAM precursors yield a most thermodynamically stable structure where the hydrophobic moiety, R, of the molecule is extended from the surface to establish normal conformational populations which permit the hydrophobic moiety of the SAM to dominate the air interface. In general, the hydrophobicity of the SAM surface increases with the value of n for the hydrophobic moiety, although in most cases sufficiently high hydrophobic properties are achieved when n is about 4 or greater and the SAM air interface is dominated by the hydrophobic moiety. The precursor can be a single molecule or a mixture of molecules with different values of n for the perfluorinated hydrophobic moiety. When the precursor is a mixture of molecules, it is preferable that the molecular weight distribution is narrow, typically a Poisson distribution or a more narrow distribution.

The SAM precursor can have a non-fluorinated hydrophobic moiety as long as it provides a sufficiently low surface energy and readily conforms to the highly partitioned surface of the uncalcined DE. Although the fluorinated SAM precursors indicated above are preferred, in some embodiments of the invention silicones and hydrocarbon equivalents, e.g., (CH$_2$)$_n$CH$_3$ or (CH(CH$_3$)OCH$_2$)$_n$CH$_2$CH$_3$, where n is 0 to 24, of the R groups of the fluorinated SAM precursors above can be used.

The surface functionalization of the DE can be carried out with the neat SAM precursor, or the precursor in a non-reactive solvent such as a hydrocarbon, an ether, or a fluorinated solvent. In some cases, the DE can have the SAM precursor deposited on the DE surface from the vapor phase. The surface functionalization can be carried out with an added non-nucleophilic proton acceptor such as a tertiary amine, for example triethylamine or pyridine, to scavenge acidic byproducts of the reaction. A catalyst can be included to accelerate the formation of the SAM. Water can also be included in the formulation if needed as determined via experimentation by one of ordinary skill in the art. The need for added water will depend upon the amount of residual water on the pretreated DE and the nature of the SAM precursor used. When water is needed it can be introduced as a liquid or a vapor. In many cases, water vapor from ambient air is sufficient to react with the SAM precursor to interconnect the precursors into the structured stable SAM coating. The time and temperature needed for effective formation of the SAM coating will depend upon the structure of the SAM precursor and any solvent, scavenger, or catalyst used. With many of the SAM precursors the treatment can be carried out rapidly at normal room temperatures. Temperatures of about 0 to about 100° C. or more can be used for application of the SAM. Reaction times can vary from as little as about 2 minutes to about 24 hours depending on the SAM precursor and conditions used for the SAM formation. In general, any excess SAM precursor and byproducts formed during deposition and bonding can be readily removed from the surface by washing or in some cases by applying a vacuum and/or heat.

The bonding of the hydrophobic coating to the DE surface can include the deposition of an intermediate layer that will chemically bond, or otherwise adhere, to the DE surface; conform to the DE topography; and bond to the hydrophobic coating applied to the intermediate layer. Generally, it is preferred to practice the invention without an intermediate layer because the deposition of two conformal coatings increases the complexity and will generally increase the cost of the deposition process.

Once the superhydrophobic DE particles are formed they can be used to generate a variety of articles, such as where they are used as discrete particles in a powder, as agglomerates, or bound to each other or to an additional substrate. The particles can be dispersed onto a surface to render that surface superhydrophobic. The superhydrophobic powder can be directly applied to many surfaces including wood products, textiles, bricks, cinder blocks, paper products, or any porous material.

Preparation of the particles into a form for attachment to a substrate can include combining the particles with a binder. The binder can be any compound that chemically or physically locks the particles to each other or a substrate as long as the binder permits the maintenance or generation of the superhydrophobic surface. The use of a binder allows attachment of the particles to nearly any surface including glasses, plastics, elastomers, metals, and ceramics. Solvents and other processing aids can be added to the binder to facilitate binding and/or direct the binder to a desired portion of the particles and/or substrates. The use of such binders permits the formation of membranes, often with a porous substrate such as a woven fabric. For example, a hydrophobic DE powder of the invention can be suspended in acetone containing a small amount of a polystyrene or polyacrylate resin as a binder. The polyacrylate can be poly(methylacrylate), poly(ethylacrylate), poly(methylmethacrylate) or any polymerized ester or acrylic acid or substituted acrylic acid. A wide variety of polymers can be used as the binder.

Figure 4:
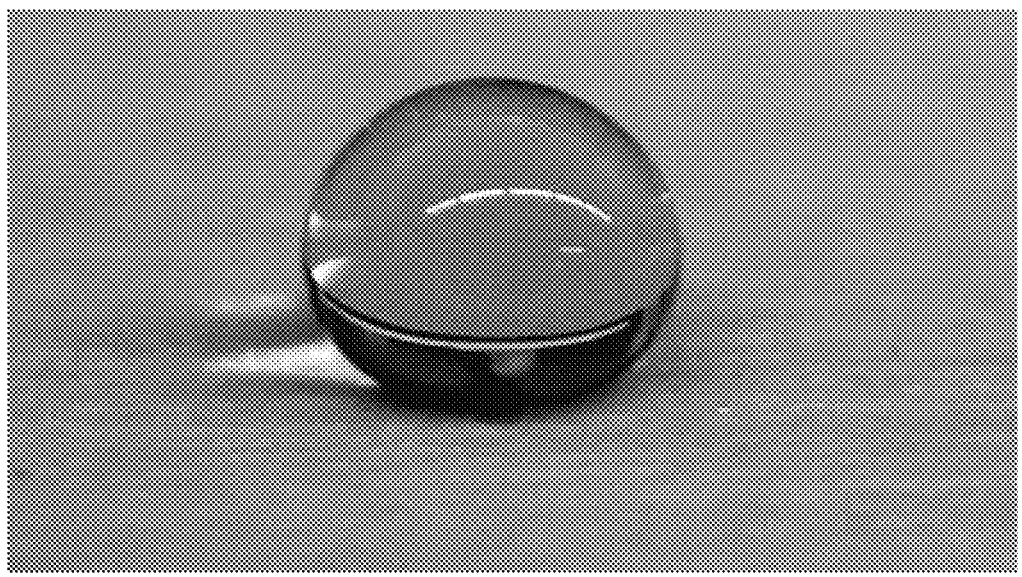
FIG. 4 is an image of a water drop on a superhydrophobic wood substrate of the invention. The wood surface was rendered superhydrophobic by depositing a coating of superhydrophobic DE particles adhered to the wood surface with a polystyrene binder.

The mixture can be painted or sprayed onto a substrate. Upon evaporation of the solvent, the superhydrophobic powder is adhered to the substrate surface by the binder, imparting a superhydrophobic surface to the substrate. A wood surface rendered superhydrophobic is shown in FIG. 4, which shows a bead of water on the surface where the contact angle is in excess of 150 degrees. The wood was rendered superhydrophobic by deposition of a suspension of superhydrophobic DE particles, where the SAM was generated from the tridecafluoro-1,1,2,2-tetrahydroctyltriclorosilane SAM precursor using a binder of polystyrene in acetone and permitting the acetone to evaporate.

While there has been shown and described what are at present considered the preferred embodiments of the invention, it will be obvious to those skilled in the art that various changes and modifications can be prepared therein without departing from the scope of the inventions defined by the appended claims.

We claim:

1. A bandage comprising:
   a substrate comprising a first surface and a plurality of coated particles,
   wherein each coated particle comprises
      a porous diatomaceous earth (DE) particle, having a highly-partitioned surface topography comprising ridges and peaks extending outwardly from the porous DE particle and
      a hydrophobic layer, continuously conforming to and covalently bonded to the surface of the porous DE particle, such that the ridges and peaks of the porous DE particle are at least partially retained,
   wherein the porous DE particle is not subjected to heat treatment in excess of 800° C.,
   wherein each coated particle is superhydrophobic.

2. The bandage of claim 1, wherein the plurality of coated particles render the first surface of the substrate superhydrophobic.

3. The bandage of claim 1, wherein the substrate is breathable.

4. The bandage of claim 1, wherein the substrate comprises a second surface that is opposite the first surface and is not superhydrophobic.

5. The bandage of claim 1, wherein the substrate comprises a second surface that is opposite the first surface and is hydrophilic.

6. The bandage of claim 1, further comprising a binder adhering the plurality of coated particles to the first surface.

7. The bandage of claim 1, wherein the plurality of coated particles are mechanically bound to the first surface.

8. The bandage of claim 1, wherein the substrate is a material selected from the group consisting of porous films, apertured films, textiles, nonwoven materials, impregnated composites thereof, and combinations thereof.

9. The bandage of claim 1, further comprising a dressing attached to the substrate.

10. The bandage of claim 9, wherein the dressing is attached to a side of the substrate opposite the first surface.

11. A method of making a bandage having a water repellant surface, comprising:
    attaching a plurality of coated particles to a first surface of a substrate to render the first surface hydrophobic,
    wherein each coated particle comprises
       a porous diatomaceous earth (DE) particle, having a highly-partitioned surface topography comprising ridges and peaks extending outwardly from the porous DE particle and
       a hydrophobic layer, continuously conforming to and covalently bonded to the surface of the porous DE particle, such that the ridges and peaks of the porous DE particle are at least partially retained,
    wherein the porous DE particle is not subjected to heat treatment in excess of 800° C.,
    wherein each coated particle is superhydrophobic.

12. The method of claim 11, wherein attaching the plurality of coated particles renders the first surface superhydrophobic.

13. The method of claim 11, wherein the attaching comprises: forming a mixture comprising the plurality of coated particles and a solvent, and applying the mixture to the first surface.

14. The method of claim 13, wherein the solvent is volatile at a temperature of the applying, and the first surface is soluble in the solvent.

15. The method of claim 11, wherein the attaching comprises:
    forming an adhesive mixture comprising the plurality of coated particles and an adhesive, and
    applying the adhesive mixture to the first surface.

16. The method of claim 11, wherein the attaching comprises: applying the plurality of coated particles to the first surface while the first surface is adherent.

17. The method of claim 11, further comprising forming the plurality of coated particles, and wherein the forming step occurs before the attaching step.

18. The method of claim 11, wherein the substrate is breathable.

19. The method of claim 11, wherein the substrate comprises a second surface opposite the first surface that is hydrophilic after the method is complete.

* * * * *